United States Patent
Cai (10) Patent No.: US 9,892,619 B2
(45) Date of Patent: Feb. 13, 2018

(54) FEEDING-BOTTLE STERILIZATION REMINDING DEVICE AND FEEDING-BOTTLE STERILIZATION REMINDING METHOD THEREOF

(71) Applicant: Jun Hao Cai, Dongguan (CN)

(72) Inventor: Jun Hao Cai, Dongguan (CN)

(*) Notice: Subject to any disclaimer, the term of this patent is extended or adjusted under 35 U.S.C. 154(b) by 0 days.

(21) Appl. No.: 15/230,376

(22) Filed: Aug. 6, 2016

(65) Prior Publication Data

US 2017/0270773 A1    Sep. 21, 2017

(30) Foreign Application Priority Data

Mar. 21, 2016   (CN) .......................... 2016 1 0162627

(51) Int. Cl.
G08B 17/00      (2006.01)
G08B 21/24      (2006.01)
A61L 2/26       (2006.01)

(52) U.S. Cl.
CPC ................ *G08B 21/24* (2013.01); *A61L 2/26* (2013.01)

(58) Field of Classification Search
CPC ............................. A61L 2202/14; A61L 2/24
See application file for complete search history.

(56) References Cited

U.S. PATENT DOCUMENTS

| | | | | |
|---|---|---|---|---|
| 4,797,661 A * | 1/1989 | Wiley | ................... | G08B 13/02 33/366.21 |
| 2010/0161150 A1* | 6/2010 | Sakurai | ................ | F02P 19/027 700/296 |
| 2015/0196676 A1* | 7/2015 | Kim | .......................... | A61L 2/07 422/119 |
| 2015/0361489 A1* | 12/2015 | Soper | ................. | G01N 27/4473 506/4 |
| 2016/0092657 A1* | 3/2016 | Nix | ....................... | G06F 19/324 705/2 |
| 2016/0097704 A1* | 4/2016 | Lin | ..................... | F02D 41/1466 73/1.06 |
| 2016/0121246 A1* | 5/2016 | Yang | ...................... | C02F 1/008 210/739 |
| 2016/0367921 A1* | 12/2016 | Pribanic | .............. | B01D 35/143 |

OTHER PUBLICATIONS

Hu Shilin et al., "On-Line Monitoring of Resistance of Aqueous Solutions At High Temperature", 1999, INIS Repository Search, total of 5 pages.*

* cited by examiner

*Primary Examiner* — Fabricio R Murillo Garcia
(74) *Attorney, Agent, or Firm* — Wayne & King LLC (57) ABSTRACT

Disclosed is a feeding-bottle sterilization reminding method, comprising the following steps: acquiring the temperature information of a current aqueous solution, and performing temperature compensation according to the temperature information; acquiring the resistance value of the aqueous solution after temperature compensation, and judging if the resistance value is within a preset threshold value, and if yes, reminding users to change water. The feeding-bottle sterilization reminding method provided in the invention is easy to operate, by collecting the water quality data in a real-time manner and comparing them with the database, and it will give a warning when the water quality is found unacceptable, to remind users to change water timely. In addition, a feeding-bottle sterilization reminding device is further disclosed in the invention.

6 Claims, 6 Drawing Sheets

FEEDING-BOTTLE STERILIZATION REMINDING DEVICE AND FEEDING-BOTTLE STERILIZATION REMINDING METHOD THEREOF

CROSS-REFERENCE TO RELATED APPLICATIONS

This application claims the priority benefit of Chinese Patent Application No. 201610162627.6 with a filing date of Mar. 21, 2016. The content of the aforementioned application, including any intervening amendments thereto, are incorporated herein by reference.

TECHNICAL FIELD

The present invention relates to the field of nursery products, and in particular, to a feeding-bottle sterilization reminding device, a circuit and a feeding-bottle sterilization reminding method.

BACKGROUND OF THE PRESENT INVENTION

The sterilization of feeding-bottles for newborns is always a concern for parents. A traditional sterilization method is to put pacifiers (or bottles, caps and other utensils for babies) in a bottle sterilizer and boil in water for a period of time, then take out and place them in a container for natural drying. After use of the feeding-bottle sterilizer for a long period of time, incrustation may produce at the bottom of the steam sterilizer due to the water quality (hard water), milk residues, dust depositions, making steam water turbid, seriously affecting the performance of the steam sterilizer and forming a potential safety hazard.

SUMMARY OF PRESENT INVENTION

In order to overcome the above shortcomings, a feeding-bottle sterilization reminding device is provided in the invention. Through detecting solution resistance with a reasonable detection circuit, the purity and cleanliness of the aqueous solution can be judged, to remind users to change water timely.

The invention provides a feeding-bottle sterilization reminding method, comprising the following steps: acquiring a temperature information of a current aqueous solution, and performing temperature compensation according to the temperature information; acquiring a resistance value of the aqueous solution after temperature compensation, judging if the resistance value is within a preset resistance threshold value, and if so, reminding users to change water.

When detecting the resistance value of the aqueous solution, a current direction of an aqueous solution electrode needs to be changed periodically.

The specific steps for the periodic change of the current direction of the aqueous solution electrode are as follows: controlling a current to flow from an A end to a B end of an aqueous solution resistor within 3/4 of a cycle T; and controlling the current to flow from the B end to the A end of the aqueous solution resistor within 1/4 of the cycle T.

When acquiring the aqueous solution, a geographical location information of the current user is firstly acquired. The preset resistance threshold is then acquired according to the geographical location information when the aqueous solution at a local position corresponding to the geographical location information is poor in water quality.

The geographical location information is acquired by a user's mobile phone, and then the preset resistance threshold of the aqueous solution at the local position corresponding to the currently acquired geographical location information is acquired via network when the water quality of the aqueous solution is poor.

Further, a feeding-bottle sterilization reminding device is provided, which includes a temperature control module, a resistance sampling module, a data processing module and a reminder module; where the data processing module is connected to the temperature control module, the resistance sampling module, and the reminder module respectively.

The temperature control module is used to feed back a temperature information of, an aqueous solution to the data processing module, and then to perform temperature compensation and adjustment according to a control information of the data processing module. The resistance sampling module collects a resistance information of the aqueous solution, and feeds back the resistance information to the data processing module.

The data processing module is used to judge if the resistance information is within a preset resistance threshold, and if yes, control the reminder module to give reminding.

The data processing module is further connected to a current control module; and the current control module is used to periodically control a direction of a current passing through an aqueous solution electrode.

The data processing module can be connected to a geographical location acquisition module, which is used to real-time acquire a geographical location information of the feeding-bottle sterilization reminding device, and acquire and invoke the preset resistance threshold when the aqueous solution at a local position corresponding to the geographical location information is poor in water quality.

The geographical location information is acquired by a user's mobile phone, and then the preset resistance threshold of the aqueous solution at the local position corresponding to the currently acquired geographical location information is acquired via network when the aqueous solution is poor in the water quality.

Compared to the prior art, the feeding-bottle sterilization reminding method provided in the invention is easy to operate, by collecting the water quality data in a real-time manner and comparing them with the database, and it will give a warning when the water quality is found unacceptable, to remind users to change water timely.

DETAILED DESCRIPTION OF PREFERRED EMBODIMENTS

After use of a feeding-bottle sterilizer for a long period of time, incrustation may produce at the bottom of the steam sterilizer due to the water quality (hard water), milk residues, dust depositions, making steam water turbid, seriously affecting the performance of the steam sterilizer and forming a potential safety hazard. The amount of water scales is correlated to the conductivity of water, thus, whether cleaning or not can be judged by measuring the conductivity of the water. However, the aqueous solution resistance is associated with the ambient temperature, the type and volume of aqueous solution, and even the test method, thus, it is particularly important to choose an appropriate test program to enhance the test accuracy.

Currently the main technical scheme for water quality detection available on the markets is to measure the water conductivity. The measurement of water conductivity is a complex electrochemical system, of which, the polarization effect, capacitance effect, temperature and ratio of solute to solvent can affect the final measurement of conductivity. At present there are several common measurement methods: bridge method, phase-sensitive detection method, frequency method, partial pressure method, transport method. The bridge method has a high requirement for the accuracy of the power sources; for the phase-sensitive detection method, it is unable to achieve the 90-degree phase difference due to the polarization effect and the capacitance effect the partial pressure method ignores the sampling resistance and the large polarization error; the transport method is unable to achieve the self-adaptive compensation for the ambient temperature and the type of solute (milk), with a low measurement accuracy.

The technical solutions are further described in details in combination with the preferred embodiments.

Figure 1:
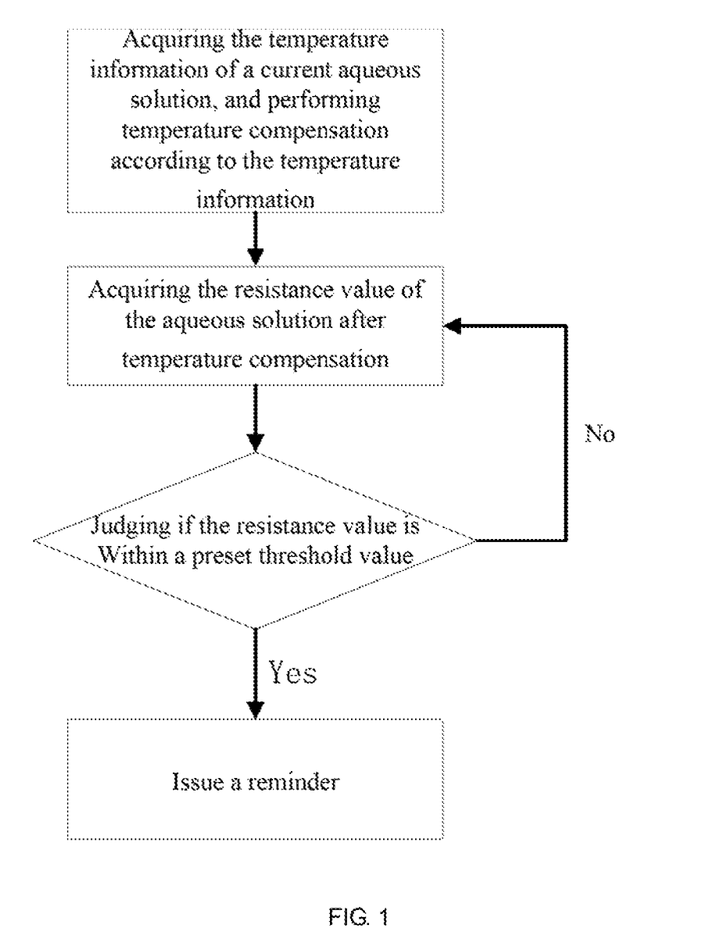
FIG. 1 shows a flow chart of a feeding-bottle sterilization reminding method according to an embodiment of the invention.
Figure 2:
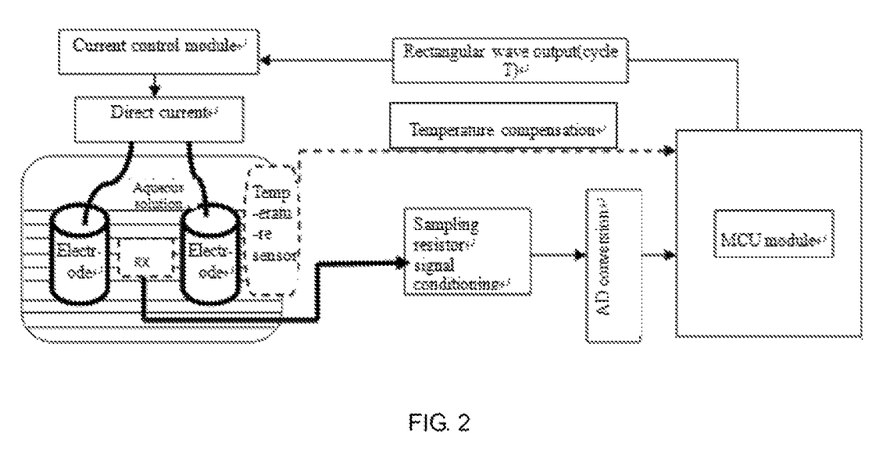
FIG. 2 shows a principle construction diagram of a feeding-bottle sterilization reminding method according to an embodiment of the invention.

Referring to FIG. 1 and FIG. 2, a feeding-bottle sterilization reminding method, comprising:

S131: acquiring the temperature information of an existing aqueous solution, and performing temperature compensation according to the temperature information.

Figure 3:
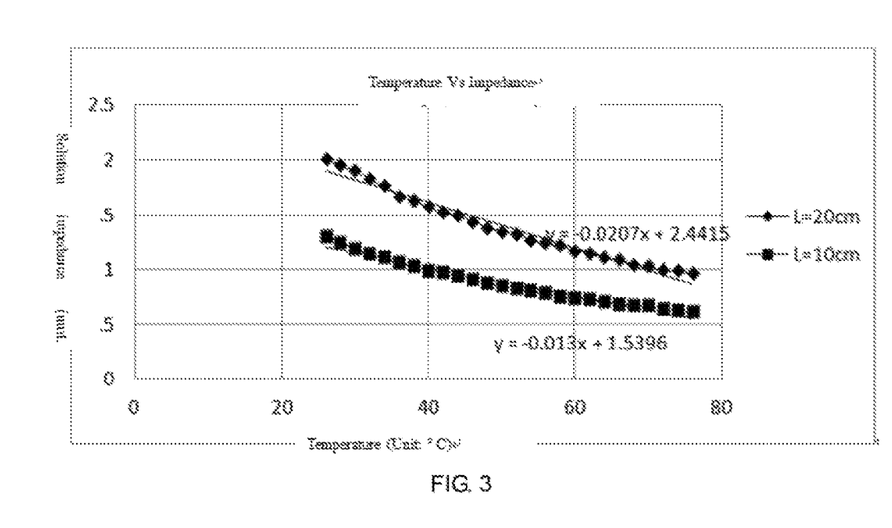
FIG. 3 shows a schematic diagram of the correlation between the temperature and aqueous solution resistance in the invention.

Since the solution temperature may affect the resistance of the solution, MCU module can collect the solution temperature information via a temperature sensor (temperature control module), then perform temperature compensation of the aqueous solution through the collected data, to get the accurate value of aqueous solution resistance effectively. The temperature compensation principle is as follows:

The resistance of an aqueous solution is associated with the temperature. FIG. 3 shows the experimental data. Real-time solution temperature compensation can be achieved by the temperature fitting function, to enhance the measurement accuracy.

For example, when the electrode distance is 10 cm and the solution temperature is 30° C., the resistance measured is 1181 ohms and when the solution temperature is 40° C., the measured value is 978 ohms, the error introduced by temperature variation between the twice measurements is (1181−978)=203 ohms, and the error rate is (978−1181)/1181=−17.2%, and the negative sign (−) indicates a decreased resistance value.

Thus, when the temperature is 40° C., the measured resistance is: $x0=40°$ C., $y0=978$ ohms, and the corresponding temperature-impedance fitting function is $$f(30)=-(0.01299*30)k\Omega+1.4976k\Omega\approx1.1097k\Omega$$

$f(x)=y=-0.01299x+b$, substituting the parameter to get $b=1.4976$ thus, substituting $x1=30°$ C., to get the resistance at 30° C.;

The real value here is 1,1812 k ohms, so the error rate is $(1.1097-1.1812)/1.1812=-6\%$, thus, the accuracy after temperature compensation is increased by 11.2%.

S102: acquiring the resistance value of the aqueous solution after temperature compensation, judging if the resistance value is within a preset resistance threshold value, and if so, reminding users to change water.

A pair of electrodes is powered on by direct current. The current passes through the solution resistor Rx. Through amplification, filtering, port security and other processing of the current signals, the resistance of the aqueous solution is acquired, then the resistance value Rx is converted to the corresponding voltage; through ADC conversion, the signal is finally sent to the MCU module (i.e. data processing module), then through the MCU data calculation and analysis, judge if the resistance value is within a preset resistance threshold value, and if so, remind users to change water; if not, give no reminder. The preset resistance threshold here is an empirical value obtained through a variety of experiments.

As a preferred embodiment, the present invention employs a bidirectional conduction conductimetric method to measure the resistance the aqueous solution.

When detecting the aqueous solution resistance, it is required to periodically control the direction of current passing through the aqueous solution electrodes. The periodical alternating of current direction can reduce the impact of the polarization effects on the circuit measurement, MCU module (i.e. data processing module) is connected to a current control module, to periodically control the direction of current in the aqueous solution. When a constant current is powered on at both ends of electrodes at a constant direction, a polarization effect will occur, greatly affecting the measured value of the solution resistance. When electrodes are placed in the water and powered on direct current, an oxidation-reduction reaction will occur on both ends of the electrodes, and the water will be electrolyzed into hydrogen and oxygen. According to the principle of galvanic cell, in the electrolysis process, electrodes and solution will form a galvanic cell, and the electrical potential of the galvanic cell is opposite to the direction of voltage applied on both ends of electrodes. Due to the presence of the electromotive force, part of the voltage externally applied is offset (equivalent to a resistor added between electrodes), that is, a chemical polarization effect. With the effect, the current between electrodes decreases, and the equivalent resistance of the solution increases. Meanwhile, during the measurement, since the excitation is applied, complex electrochemical reaction occurs close to electrodes and electron exchanges occur, leading to rapid loss of ions in the solution. Since the speed of loss of ions in the solution close to the electrodes is much faster than the speed of supplementing electrons from the solution far from the electrodes, a potential difference between the solution close to the electrodes and the external solution occurs, and this process is known as concentration polarization.

Figure 4:
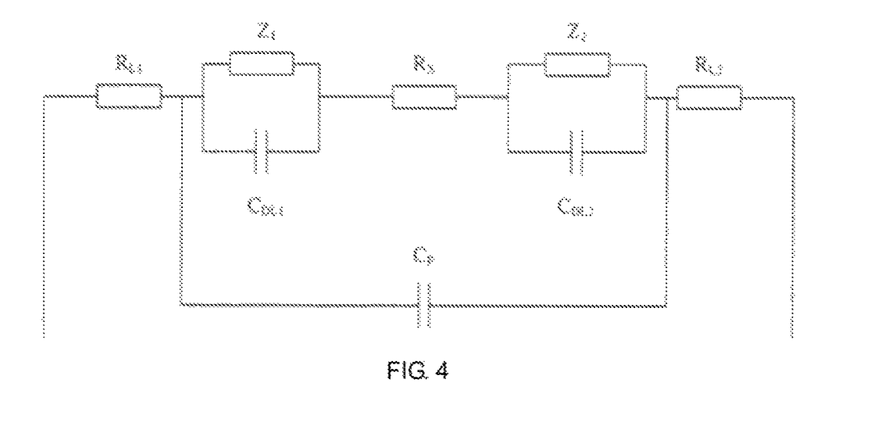
FIG. 4 shows an equivalent circuit diagram of an aqueous solution in the invention.

FIG. 4 shows the equivalent circuit diagram of an aqueous solution in the invention.

Wherein, RX is the solution resistor. Due to the polarization effect between the solution and two electrodes, an equivalent circuit Z1, CDL1 and Z2, CDL2 forms, and the circuit structure is in a parallel form (of which, CDL1, CDL2 are double-layer capacitors, and Z1, Z2 are impedances formed by polarization effect). The two groups of equivalent circuits are connected with RX in series; the solution reciprocates under the action of the excitation signals to form an equivalent capacitor CP, which is called electrolytic capacitor. CP is connected with the above in parallel; when the measurement accuracy is high, the lead resistors connected to two electrodes (RL1, RL2) must be considered, which are connected in series with the above equivalent parallel circuit, If an alternating current is powered on at both ends of the electrodes, appropriate AC excitation voltage signals are selected. To facilitate the analysis, it is considered that RL1, RL2, Z1, Z2, CDL1 CDL2 have a small impact on the resistance value of the solution, i.e. Z1, Z2, CDL1, CDL2 are approximately equal to 0; in addition, the lead resistors connected to two electrodes (RL1, RL2) are small enough (approximately equal to 0). After the parameters with less influence are ignored, the overall equivalent circuit as shown in FIG. 3 is obtained (of which, CP is electrolytic capacitor of the solution, with an order of μF).

Figure 5:
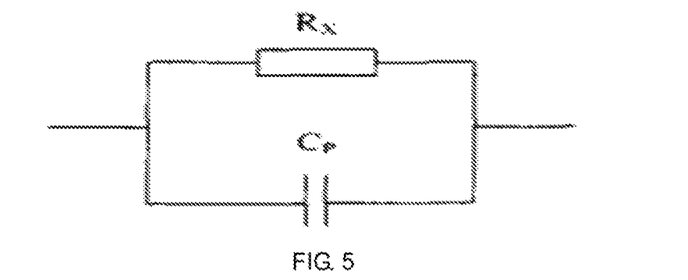
FIG. 5 shows equivalent circuit diagram of an aqueous solution after switching on alternating current in the invention.

However, if an alternating current (such as a sine wave) is used as the power source for measurement of the solution, the polarization effect can be eliminated and the life of the electrode can be prolonged. The measurement resistor and the capacitor are connected in parallel in the equivalent circuit of solution in FIG. 5, in order to avoid the effect of the capacitor on the measurement accuracy, DC can be used as the power source of measurement of the solution. However, the DC may bring polarization effect, the values of Z1, Z2, CDL1, CDL2 can not be ignored, which will bring a great error and increase the difficulty of calculation and analysis.

In order to solve the above problems, the technical solution employs a bidirectional conduction conductimetric method, which can eliminate the effect of capacitance effect of electrodes on the measurement results and greatly reduce the influence of polarization effect, besides, with the parameter compensations of micro control unit such as temperature, type of aqueous solution, it can achieve high accuracy and stability.

To reduce the influence of polarization effect on the measurement circuit, an alternating current at certain frequency is powered on at both ends of electrodes. Using the bidirectional conduction conductimetric method, a current control module is employed to control the DC power supply to stably output a current with a rectangular wave, equivalent to AC of rectangular wave. During operation, MCU module will always output a rectangular wave with cycle T which is input to the current direction control module, to change the direction of current between the electrodes at both ends. The current flows through the solution resistor from an A end to a B end within ¾ of the cycle T, and flows from the B end to the A end within ¼ of the cycle T. Of course, the time can be adjusted according to different current and voltage or other environments, for example, ⅔ T and ⅓ T. Since Cp is connected with Rx in parallel, Cp may form certain impedance if a rectangular wave alternating current is powered on, and bring error for the measurement results. Multiple analyses of experimental data show that when the cycle T of the rectangular wave is 1 ms, i.e. the frequency is 10 k, the error produced by Cp is minimum. Therefore, the frequency of rectangular waves output from MCU module is set at 1K.

The technical solution employs a bidirectional conduction conductimetric method, which can eliminate the effect of capacitance effect of electrodes on the measurement results and greatly reduce the influence of polarization effect, besides, with the parameter compensations of micro control unit such as temperature, type of aqueous solution, it can achieve high accuracy and stability.

Parents who use feeding-bottle sterilization reminding devices in daily life are across the country. The water quality standard in different regions is different. The impurities of tap water in Guangzhou are totally different from those in Beijing, and the resistance of aqueous solution measured is different, therefore, users in each region should detect the resistance of the local tap water and record the corresponding water purity, then according to the resistance value of the local aqueous solution, obtain the resistance threshold through experiments when the water quality is poor. As a preferred embodiment, a geographical location acquisition module is provided in a feeding-bottle sterilization reminding device, to acquire the geographical location information of the current feeding-bottle sterilization reminding device, and acquire the resistance threshold of the local aqueous solution when the water quality is poor according to the geographical location information. When the aqueous solution is not clean, the detected resistance no more than its resistance threshold, reminding users to change water.

However, if the geographical location information acquisition function is added to a feeding-bottle sterilization reminding device, it will greatly enhance the cost of the whole product. A Bluetooth or other wireless network devices can used to connect this device with user's mobile phone. Users can acquire the current geographical location information using their mobile phones, and then acquire the current preset resistance threshold corresponding to the current geographical location information via the network when the water quality of the aqueous solution at the local position corresponding to the geographical location information is poor, to greatly reduce the cost of the product.

Figure 6:
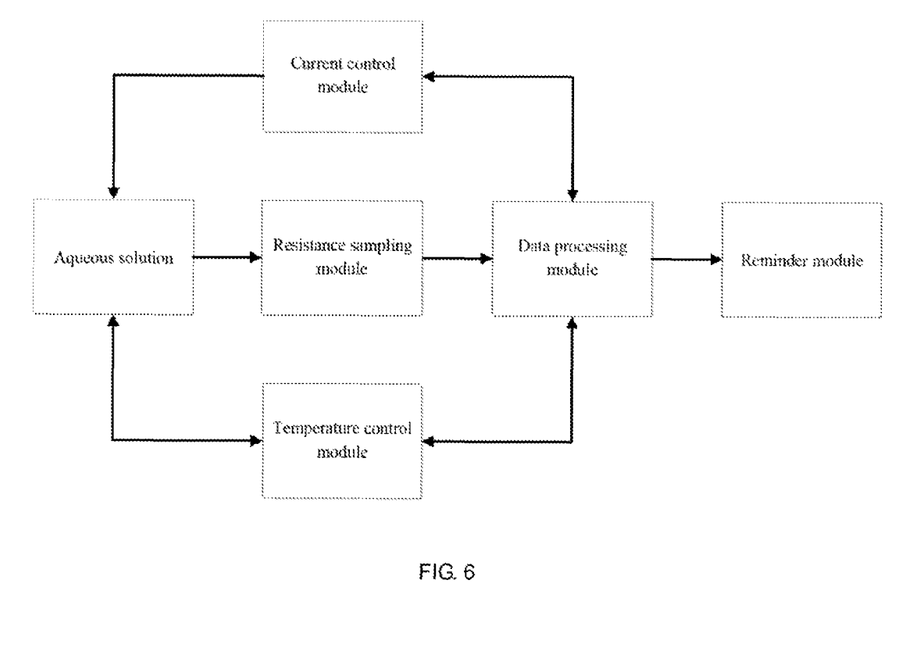
FIG. 6 shows a schematic diagram of a feeding-bottle sterilization reminding device according to an embodiment of the invention.

FIG. 6 shows a schematic diagram of a feeding-bottle sterilization reminding device according to an embodiment of the invention.

A feeding-bottle sterilization reminding device, comprising a temperature control module, a resistance sampling module, a data processing module and a reminder module; wherein the data processing module is connected to the temperature control module, the resistance sampling module, and the reminder module respectively.

The temperature control module is used to feed back the temperature information of aqueous solution to the data processing module, and then perform temperature compensation and adjustment according to the control information of the data processing module. The resistance sampling module collects the resistance information of the aqueous solution, and feeds back the resistance information to the data processing module;

The data processing module is used to judge if the resistance information is within the preset resistance threshold, and if yes control the reminder module to give reminding.

As a preferred embodiment, the data processing module can be further connected to a current control module; and the current control module is used to periodically control the direction of a current passing through an aqueous solution electrode. Through the periodic alternating of the current direction, it can reduce the influence of polarization effect on the measurement circuit in addition, a geographical location acquisition module provided in the feeding-bottle sterilization reminding device, which is used to real-time acquire the geographical location information of the current, feeding-bottle sterilization reminding device, and acquire and invoke the preset resistance threshold when the local water quality of the aqueous solution is poor. When the aqueous solution is unclean and the resistance of aqueous solution detected no more than its preset resistance threshold, remind users to change water.

However, if the geographical location information acquisition function is added to a feeding-bottle sterilization reminding device, it will greatly enhance the cost of the whole product. A Bluetooth or other wireless network devices can used to connect this device with the user's mobile phone. Users can acquire the current geographical location information using their mobile phones, and then acquire the current preset resistance threshold corresponding to the currently acquired geographical location information via the network when the local water quality of aqueous solution is poor, to greatly reduce the cost of the product.

In this embodiment, the operating principle of various modules is consistent with the methods in the invention, and it is not described again.

The above embodiments only describe several kinds of mode of execution with details, but it cannot be understood to limit the scope of the present invention patent. It should be noted that for ordinary technicians skilled in the art, modifications and improvements can be made without departing from the concept of the invention, and all of them fall within the scope of protection in the invention. Accordingly, the scope of protection of the invention should be subject to the claims.

I claim:

1. A feeding-bottle sterilization reminding method, comprising the following steps:
   acquiring a temperature information of a current aqueous solution inside a feeding-bottle, and performing temperature compensation according to the temperature information;
   acquiring a resistance value of the aqueous solution after the temperature compensation and judging if the resistance value is within a preset resistance threshold value, and if so, reminding a user to change water of the feeding-bottle;
   wherein a current direction of an aqueous solution electrode needs to be changed periodically when detecting the resistance value of the aqueous solution;
   wherein periodically changing of the current direction of the aqueous solution electrode comprises:
      controlling a current to flow from an A end to a B end of an aqueous solution resistor within ¾ of a cycle T; and
      controlling the current flow from the B end to the A end of the aqueous solution resistor within ¼ of the cycle T.

2. The feeding-bottle sterilization reminding method according to claim 1, wherein further comprising:
   acquiring a current geographical location information of the user when acquiring the aqueous solution: and
   a geographical location information of the current user when acquiring the aqueous solution; and acquiring the preset resistance threshold value according to the geographical location information when the aqueous solution at a local position corresponding to the geographical location information is poor in water quality.

3. The feeding-bottle sterilization reminding method according to claim 2, wherein the geographical location information is acquired by a mobile phone of the user, and then the preset resistance threshold value of the aqueous solution at the location position corresponding to the currently acquired geographical location information is acquired via a network when the aqueous solution is poor in the water quality.

4. A feeding-bottle sterilization reminding device, comprising a temperature control module, a resistance sampling module, a data processing module and a reminder module;
   wherein the data processing module is connected to the temperature control module, the resistance sampling module, and the reminder module respectively;
   the temperature control module is configured to feed back a temperature information of an aqueous solution inside a feeding-bottle to the data processing module, then the temperature control module is further configured to perform temperature compensation and adjustment according to a control information of the data processing module;
   the resistance sampling module is configured to collect a resistance information of the aqueous solution, and feeds back the resistance information to the data processing module;
   the data processing module is configured to judge if the resistance information is within a preset resistance threshold, and if yes, control the reminder module to give reminding to a user about changing water of the feeding-bottle;
   wherein the data processing module is further connected a current control module; and
   the current control module is configured to periodically control and change a direction of a current passing through an aqueous solution electrode when the resistance sampling module collects the resistance information;
   wherein for periodically control and change the direction of the current passing through the aqueous solution electrode, the data processing module is further configured to:
      control and change the current to flow from an A end to a B end of an aqueous solution resistor within ¾ of a cycle T; and
      control and change the current to flow from the B end to the A end of the aqueous solution resistor within ¼ of the cycle T.

5. The feeding-bottle sterilization reminding device according to claim 4, wherein the data processing module is connected to a geographical location acquisition module, which is used to real-time acquire a geographical location information of the feeding-bottle sterilization reminding device, and to acquire and invoke the preset resistance threshold when the aqueous solution at a local position corresponding to the geographical location information is poor in water quality.

6. The feeding-bottle sterilization reminding device according to claim 5, wherein the geographical location information is acquired by a mobile phone of a user, and then the preset resistance threshold of the aqueous solution at the local position corresponding to the real-time acquired geographical location information is acquired via network when the aqueous solution is poor in the water quality.

* * * * *